US00PP18327P2

(12) United States Plant Patent
Jensen

(10) Patent No.: US PP18,327 P2
(45) Date of Patent: Dec. 18, 2007

(54) ***CAMPANULA* PLANT NAMED 'PKMP06'**

(50) Latin Name: *Campanula portenschlagiana*
Varietal Denomination: PKMP06

(75) Inventor: Gert Kim Jensen, Odense N (DK)

(73) Assignee: Gartneriet PKM A/S, Odense N (DK)

( * ) Notice: Subject to any disclaimer, the term of this patent is extended or adjusted under 35 U.S.C. 154(b) by 0 days.

(21) Appl. No.: 11/455,820

(22) Filed: Jun. 20, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

Print–out of application number and filing date from European Union–Community Plant Variety Office (CPVO) website (www.cpvo.fr) for corresponding, international PBR application, CPVO 2006/1003 filed Apr. 25, 2006.*

Print–out of application number and filing date from Canadian Food Inspection Agency–Plant Breeder's Right Office (CPVO) website (www.inspection.gc.ca) for corresponding, Canadian PBR application number 06–5478 filed May 17, 2006.*

* cited by examiner

*Primary Examiner*—Kent Bell
*Assistant Examiner*—June Hwu
(74) *Attorney, Agent, or Firm*—Foley & Lardner, LLP

(57) ABSTRACT

A new and distinct cultivar of *Campanula* plant named 'PKMP06', characterized by having upright plant habit; dense and bushy plant form, mainly due to more upright stems; vigorous growth habit, and less need for chemical growth retardation; more uniform and white flower color; and no need for vernalization.

4 Drawing Sheets

Latin name of genus and species of the plant claimed: *Campanula portenschlagiana.*
Variety denomination: 'PKMP06'.

BACKGROUND OF THE INVENTION

The present invention relates to a new and distinct cultivar of *Campanula* plant, botanically known as *Campanula portenschlagiana schult.,* commonly known as Bellflower, and hereinafter referred to by the name 'PKMP06'.

The new *Campanula,* 'PKMP06', is a product of a planned breeding program conducted by the inventor, Gert K. Jensen, in Søhus, Denmark. The objective of the breeding program is to develop a new *Campanula* cultivar with uniform and compact plant form and white flowers.

The new *Campanula* cultivar originated from a cross made in 2003 by the inventor between a proprietary selection of *Campanula portenschlagiana schult.* designated '08.03.322' as the female parent (unpatented) and a proprietary selection of *Campanula portenschlagiana schult* designated '08.03.3094' as the male parent (unpatented). The inventor selected the new *Campanula* cultivar from the progeny of the above cross in 2003 on the basis of its compact and freely flowering habit. Plants of the new *Campanula* are more upright, compact and more freely flowering than plants of both parental cultivars.

Asexual reproduction of the new *Campanula* cultivar by terminal cuttings taken and propagated since Jan. 1, 2006 in Søhus, Denmark, has shown that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMP06'. These characteristics in combination distinguish 'PKMP06' as a new and distinct cultivar:

1. Upright plant habit;
2. Dense and bushy plant form, mainly due to more upright stems;
3. Vigorous growth habit, and less need for chemical growth retardation;
4. More uniform and white flower color; and
5. No need for vernalization.

Side-by-side comparisons between the instant plant and the parental cultivars, '08.03.322' and '08.03.3094', were conducted by the inventor in Søhus, Denmark. Plants of 'PKMP06' differ from the cultivars '08.03.322' and '08.03.3094' in the following characteristics:

1. Plants of 'PKMP06' have longer internodes than plants of the cultivars '08.03.322' and '08.03.3094'.
2. Plants of 'PKMP06' have darker grey green-colored leaves whereas plants of the cultivars '08.03.322' and '08.03.3094' have green-colored leaves.
3. Plant of 'PKMP06' are more compact and upright than the cultivars '08.03.322' and '08.03.3094'.

BRIEF DESCRIPTION OF THE PHOTOGRAPHS

The accompanying colored photographs illustrate the overall appearance of the new cultivar 'PKMP06', showing the colors as true as it is reasonably possible to obtain in colored reproductions of this type. Colors in the photographs may differ slightly from the color values cited in the detailed botanical description, which more accurately describe the actual colors of 'PKMP06'.

DETAILED BOTANICAL DESCRIPTION

Figure 1:
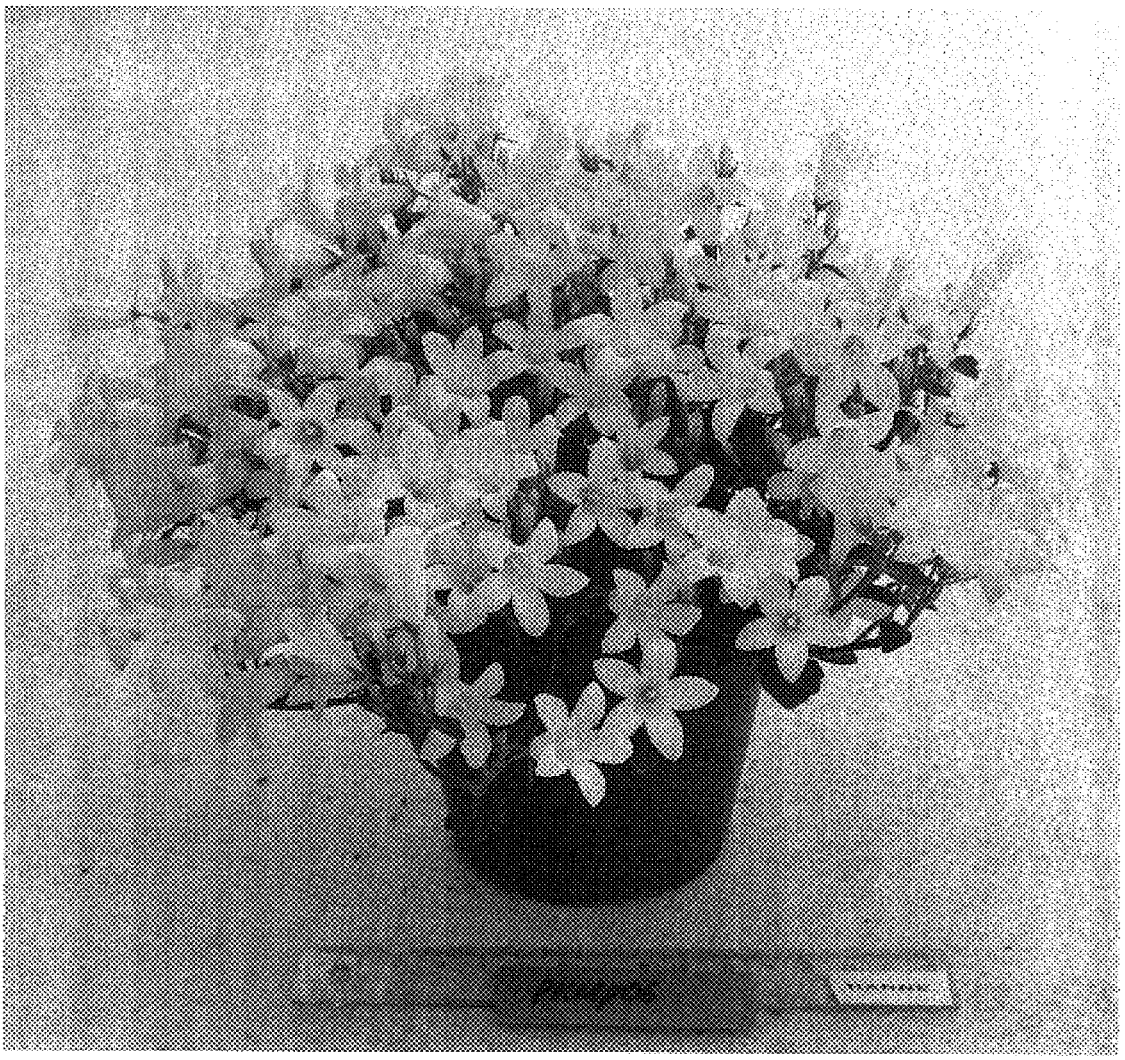
FIG. 1 shows a side perspective view of a typical flowering plant of 'PKMP06', as grown in a 10.5 cm pot.
Figure 2:
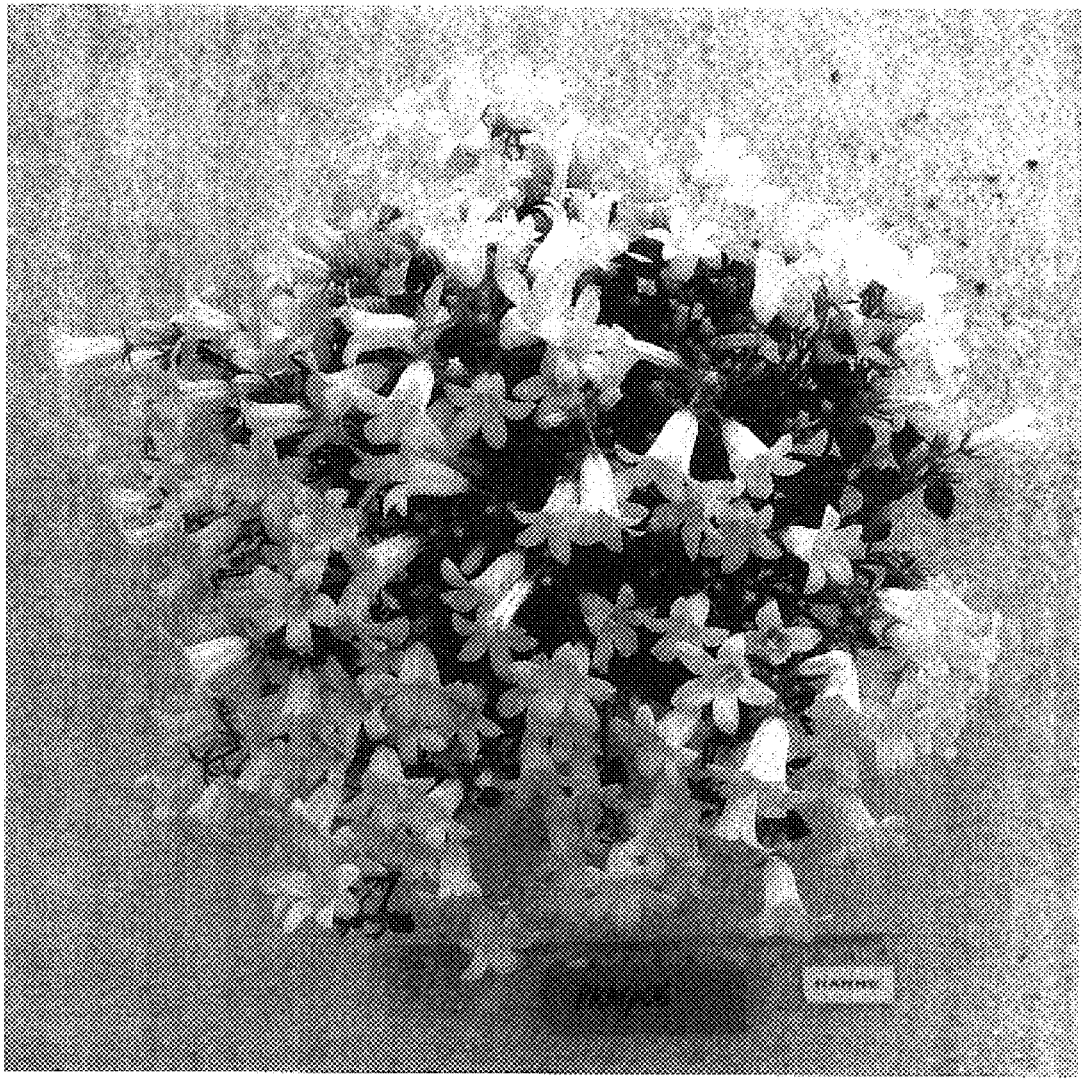
FIG. 2 shows a top perspective view of a typical flowering plant of 'PKMP06', as grown in a 10.5 cm pot.
Figure 3:
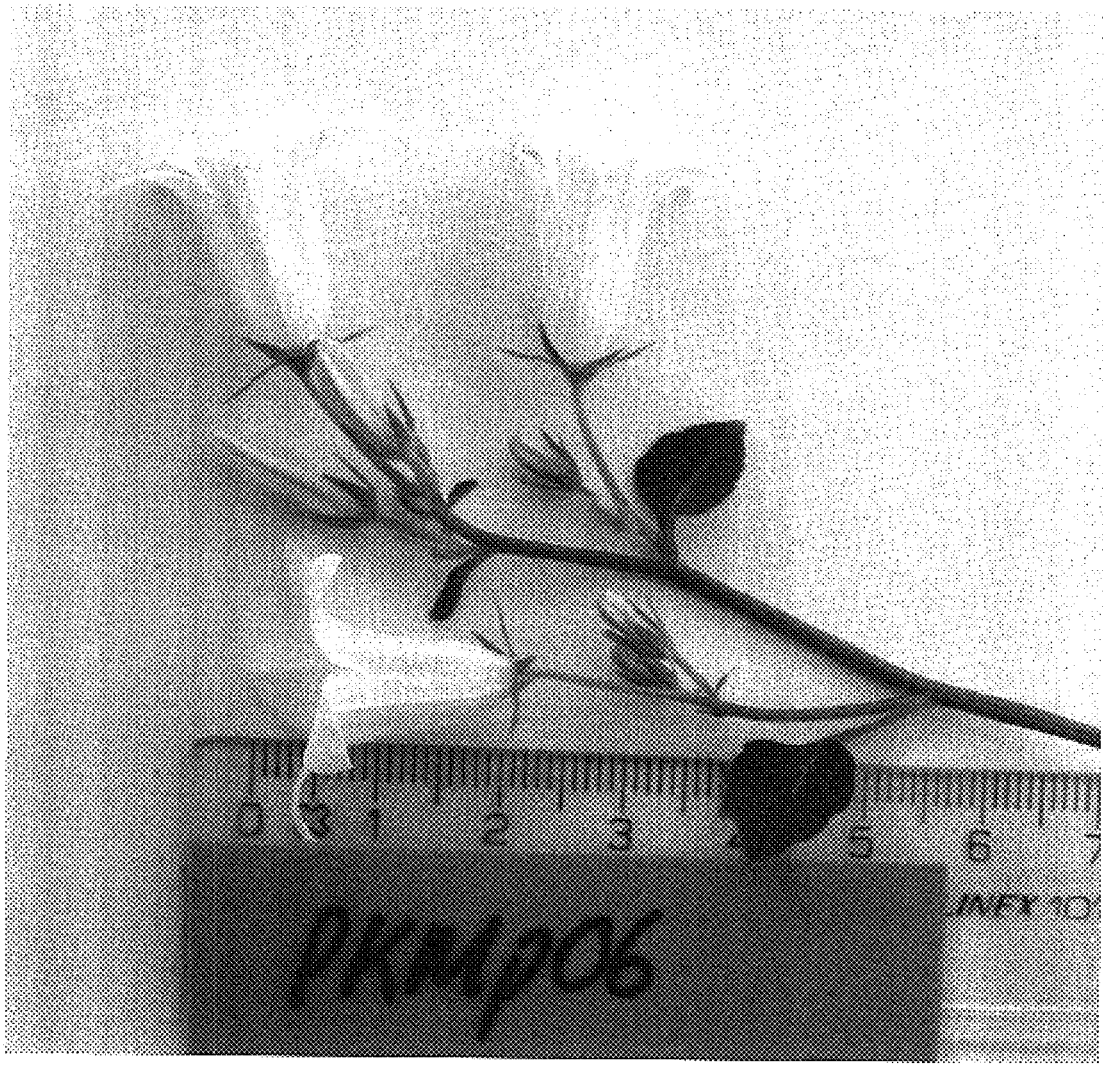
FIGS. 3 and 4 show a close-up view of typical flowering racemes and leaves of 'PKMP06'.
Figure 4:
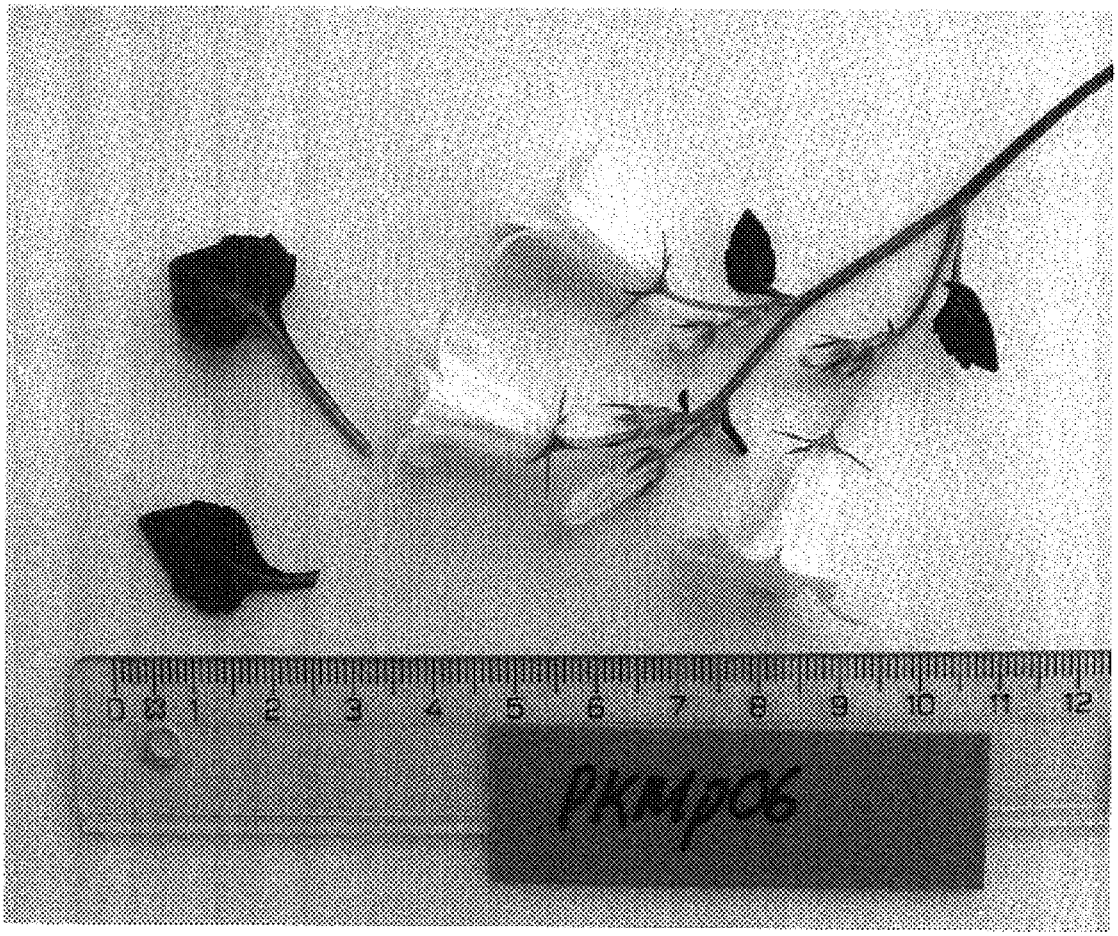

The new *Campanula* cultivar 'PKMP06' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* cultivar 'PKMP06' as grown in a heated and lighted, glass-covered greenhouse in Søhus, Denmark, under conditions which closely approximate those generally used in commercial practice where day temperatures in the greenhouse range from 18–20° C. and the night temperatures range from 16–18° C. Ambient light levels used while growing plants of 'PKMP06' are +45 $Wm^2$. Plants of 'PKMP06' are grown with 16 to 18 hour long day photoperiodic treatments from the tenth week.

The age of the 'PKMP06' plants described is 14 weeks old (after cutting, being pinched twice, but not retarded) and grown in 10.5 cm pots. The photographs and descriptions were taken during the winter season when day temperatures in glass-covered greenhouse range from 18–20° C. and when night average temperatures in glass-covered greenhouse range from 16–18° C.

Color references are made to The Royal Horticultural Society Color Chart (R.H.S.), $4^{th}$ edition, except where general colors of ordinary significance are used.

Classification:
Botanical: *Campanula portenschlagiana.*
Parentage:
Female parent: *Campanula portenschlagiana schult.* designated '08.03.322' (unpatented).
Male parent: *Campanula portenschlagiana schult.* designated '08.03.3094' (unpatented).
Propagation:
Type cutting: Terminal vegetative cuttings.
Time to initiate roots: About 10 to 14 days at 18 to 21° C. in tunnels in a greenhouse.
Root description: Fine, well branched.
Plant description:
Form: Perennial rosette plant with upright plant habit. Campanulate flowers in racemes. Freely branching with lateral branches forming at every node; dense and bushy.
Crop time: After rooting, about 14 weeks are required to produce finished flowering plants in 10.5 cm pots.
Vigor: Vigorous growth rate.
Plant height (soil level to top of plant plane): About 10 cm.
Plant spread (width): About 27 cm.
Lateral branches: Quantity: About 85–90 per plant. Length (including flowers): 11 cm to 13 cm. Diameter: About 1 mm to 2 mm. About 5 leaves per lateral branch.
Internode length: 1.5 cm to 2.5 cm.
Stem: Shape: Found. Strength: Soft. Aspect: Center — ascending; Perimeter: spreading to drooping. Pubescence: Short hairs, hispidulous. Color: RHS 143B, green.
Foliage description: Leaves alternate and single, cordate — slightly dentate shape, and reticulated venation.
*Length.*—Basal: About 15 mm to 20 mm. Apical: About 4 mm to 5 mm.
*Width.*—Basal: About 25 mm to 30 mm. Apical: About 2 mm to 3 mm.
*Overall shape.*—Cordate, slightly dentate.
*Apex.*—Rounded.
*Base.*—Cordate.
*Margin.*—Undulating, dentate.
*Texture.*—Upper surface: Smooth, glabrous, dull.
*Pubescence.*—Lower surface: Hispidulous, dull.
*Color* (*immature and mature foliage*).—Both surfaces: RHS N138B, green.
*Venation.*—Color (both surfaces): RHS 138B, green. Pattern: Reticulate.
Petiole:
*Length.*—Basal: 4 cm to 5 cm. Apical: Up to 1.0 cm.
*Diameter.*—0.5 to 1.0 mm.
*Color.*—RHS 138B, green.
Flower description:
Flower arrangement and shape: Upright to spreading, campanulate, acropetal flowers in racemes. Flowers with small star shaped calyx.
Natural flowering season: Continuous throughout the spring and summer. Season can be extended by long day treatments. No vernalization needed.
Flower longevity: On the plant, flowers last about 5 to 9 days; however, longevity of individual flowers is highly dependent on temperature and light conditions. Flowers persistent.
Time to flower: About 40 long days.
Fragrance: None.
Inflorescence size:
*Length.*—About 6 cm to 10 cm.
*Diameter.*—About 25 cm.
Number of flowers per inflorescence: About 9.
Number of flowers per lateral stem: 10 to 20.
Number of flowers and buds per plant: About 1500.
Flowers:
*Length.*—About 17 mm.
*Diameter.*—About 25 mm.
*Acute petal lobes.*—8–10 mm long and 7 mm wide at base. Petal color, fully opened, RHS 155D, white.
Buds:
*Length.*—Up to 15 mm.
*Diameter.*—Up to 4 mm.
*Shape.*—Oblong, with ridges.
*Color.*—RHS 143C, green, to RHS 155D, white.
Petals:
*Arrangement.*—Single, sympetalous, campanulate.
*Quantity per flower.*—About 5.
*Length.*—About 8 mm to 10 mm.
*Width.*—About 7 mm.
*Overall shape.*—Arrow-shaped.
*Tip.*—Acute.
*Base.*—Fused.
*Margin.*—Entire.
*Texture.*—Velvety.
*Color* (*when opening*).—Upper surface RHS N155D, white, and Under surface RHS 155D, white.

*Color* (*when opened*).—Upper and under surfaces, RHS 155D, white.

*Fading.*—No fading, withering.

Sepals:

*Arrangement.*—Free.

*Appearance.*—Shiny, glabrous.

*Quantity per flower.*—5.

*Length.*—About 3 mm to 5 mm.

*Width.*—About 1 mm.

*Overall shape.*—Arrow-shaped.

*Tip.*—Cuspidate.

*Base.*—Fused.

*Margin.*—Entire.

*Texture.*—Smooth.

*Color* (*immature*).—Upper and under surfaces, RHS 144B, yellow-green.

*Color* (*mature*).—Upper and under surfaces: RHS 138A, green.

Peduncles:

*Length.*—About 20 mm to 38 mm.

*Diameter.*—About 1 mm.

*Strength.*—Average.

*Angle.*—Varies.

*Color.*—Same as stem, RHS 143B, green.

Reproductive organs:

Androecium:

*Stamen.*—Quantity: 5, fused until pollen has been shed.

*Anther.*—Shape: Fused, after shedding curling. Length: About 1 mm. Color: RHS 158D, yellow-white.

*Pollen.*—Amount: Moderate. Color: RHS 158D, yellow-white.

Gynoecium:

*Pistil.*—Quantity: 1. Length: About 12 mm.

*Stigma.*—Shape: Tripartite. Color: RHS 155D, white.

*Style.*—Length: About 11 mm. Color: RHS 155D, white.

*Ovary.*—Color: RHS 155D, white.

Seeds:

*Quantity.*—About 25 per flower.

*Length.*—About 1 mm.

*Diameter.*—1 mm.

*Texture.*—Glabrous, hard.

*Color.*—RHS 199C, grey-brown.

Growth retardants: Bonzi.

Weather tolerance: Plants of the new *Campanula* have exhibited good tolerance to drought, rain and wind, with low temperature resistance to −15° C.

Disease/pest resistance: 'PKMP06' is not resistant to any diseases or pests typical to *Campanula* cultivars.

Disease/pest susceptibility: 'PKMP06' is susceptible to *Botrytis.*

I claim:

1. A new and distinct cultivar of *Campanula* plant named 'PKMP06', as illustrated and described herein.

* * * * *